(12) United States Patent
Stolc et al.

(10) Patent No.: US 7,949,472 B1
(45) Date of Patent: May 24, 2011

(54) RAPID POLYMER SEQUENCER

(75) Inventors: Viktor Stolc, Milpitas, CA (US);
Mathew W. Brock, San Francisco, CA (US)

(73) Assignee: The United States of America as represented by the National Aeronautics and Space Administration, Washington, DC (US)

( * ) Notice: Subject to any disclaimer, the term of this patent is extended or adjusted under 35 U.S.C. 154(b) by 1183 days.

(21) Appl. No.: 10/885,537

(22) Filed: Jun. 24, 2004

(51) Int. Cl.
*G01N 33/48* (2006.01)
*C12M 1/00* (2006.01)
*G06G 7/58* (2006.01)

(52) U.S. Cl. .......................... 702/19; 435/283.1; 703/12

(58) Field of Classification Search .................. None
See application file for complete search history.

(56) References Cited

U.S. PATENT DOCUMENTS

| | | | | |
|---|---|---|---|---|
| 6,740,518 | B1 * | 5/2004 | Duong et al. | 435/287.2 |
| 7,258,838 | B2 * | 8/2007 | Li et al. | 422/68.1 |
| 2002/0094526 | A1 * | 7/2002 | Bayley et al. | 435/6 |

OTHER PUBLICATIONS

Akeson, et al., Microsecond Time-Scale Discrimination Among Polycytidylic Acid, Polyadenylic Aci . . . , Biophysical Journal, Dec. 1999, 3227-3233, 77, Biophysical Society.
Blodgett, Films Built by Depositing Successive Monomolecular Layers on.A Solid Surface, Journal of American Chemical Society, 1935, 1007-1022, 57.
Chechik, et al., Reactions and Reactivity in Self-Assembled Monolayers, Advanced Materials, 2000, 1161-1171, 12-16, Wiley-VCH.
Kasianowicz, et al., Characterization of individual polynucleotide molecules using a membrane channel, Proc. Natl. Acad. Sci., Nov. 1996, 13770-13773, 93.
Lahann, et al., A Reversibly Switching Surface, Science, 2003, 371-374, 299.
Langmuir, The Constitution and fundamental Properties of Solids and Liquids. II. Liquids, J. Amer. Chem. Soc., 1917, 1848-1906, 39.
Li, et al., Ion-beam sculpting at nanometre length scales, Letters to Nature, 2001, 166-169, 412, Macmillan Magazines Ltd.
Marziali, et al., New DNA Sequencing Methods, Annu. Rev. Biomed. Eng., 2001, 195-223, 3, Annual Reviews.
Sagiv, Organized Monolayers by Adsorption. 1. Formation and Structure Oleophobic Mixed Monolayers on S . . . , J. Amer. Chem. Soc., 1980, 92-98, 102, American Chemical Society.
Stein, et al., Ion-Beam Sculpting Time Scales, Physical Review Letters, 2002, 276106-1-276106-4, 89-27, The American Physical Society.

* cited by examiner

*Primary Examiner* — Eric S Dejong
(74) *Attorney, Agent, or Firm* — John F. Schipper; Robert M. Padilla (57) ABSTRACT

Method and system for rapid and accurate determination of each of a sequence of unknown polymer components, such as nucleic acid components. A self-assembling monolayer of a selected substance is optionally provided on an interior surface of a pipette tip, and the interior surface is immersed in a selected liquid. A selected electrical field is impressed in a longitudinal or transverse direction at the tip, a polymer sequence is passed through the tip, and a change in an electrical current signal is measured as each polymer component passes through the tip. Each measured change in electrical current signals is compared with a database of reference signals, with each reference signal identified with a polymer component, to identify the unknown polymer component. The tip preferably has a pore inner diameter of no more than about 40 nm and is prepared by heating and pulling a very small section of a glass tubing.

24 Claims, 9 Drawing Sheets

Fig. 2A (Polymer Absent)

RAPID POLYMER SEQUENCER

ORIGIN OF THE INVENTION

The invention described herein was made, in part, by an employee of the United States Government and may be manufactured and used by or for the Government for governmental purposes without the payment of any royalties thereon or therefor.

TECHNICAL FIELD

The present invention is a method and system for rapidly and accurately determining an ordered sequence of molecular units, such as bases in a nucleic acid, such as DNA or RNA, and for fabricating a nanopore system to facilitate the sequencing.

BACKGROUND OF THE INVENTION

Nanofabrication techniques offer the possibility to create solid state pores or apertures with diameters and lengths similar to diameters and lengths of single nucleotides or proteins. Solid state nanopores permit use of non-physiological conditions for structural manipulation of biopolymers, such as non-neutral pH levels, high temperatures and/or high voltage differences. Use of a solid state substrate will allow a more straightforward manipulation of surface chemistry in the pore, which may be critical to fine-tune the rate of nucleic acid translocation or the degree of ionic current reduction associated with passage of a polymer, such as a poly-nucleotide through a nanopore.

Kasianowicz et al, in "Characterization of individual polynucleotide molecules through a membrane channel," Proc. Nat. Acad. Sci. vol. 93 (1996) 195-223, have used a pore of diameter about 1.5 nanometers (nm) in the bacterial $\alpha$-hemolysin ion channel protein, and have applied an electrical field to drive a negatively charged polynucleotide through the pore from one side to the other, which transiently reduces ionic conductance through the pore. Akeson et al, in "Microsecond Time Scale Discrimination Among Polycytidylic Acis in Homopolymers or as Segments Within Single RNA Molecules," Biophys. Jour. Vol. 77 (1999) 3227-3233, have shown that polynucleotides of different lengths can be discriminated by time duration of translocation as the nucleotide sequence passes through a pore. Translocation of different nucleotide homopolymers reduces ionic conductance of $\alpha$-hemolysin by characteristic amounts, which suggests that the individual nucleotides in a heteropolymer could be identified, if passed through a nanopore of appropriate dimensions and composition. However, $\alpha$-hemolysin has a pore length as long as a sequence of about 20 nucleotides so that discrimination between individual nucleotides using $\alpha$-hemolysin is not possible.

What is needed is a system that provides rapid and accurate identification of ordered components of a nucleic acid, protein or similar polymer, at rates up to and above one component per μsec. Preferably, the approach should adequately discriminate between the different ordered components present in the polymer and provide accurate ordering, with an acceptable error rate that is controllable by varying the rate at which the polymer components pass through and is read by the system.

SUMMARY OF THE INVENTION

These needs are met by the invention, which provides a system and associated method that relies upon a pore at a pipette tip, having a pore diameter as small as 1-40 nm, preferably containing a selected alkali halide, ammonium compound (e.g., $NH_4$, $N(CH_3)_4$, or a suitable ionic organic compound or ionic inorganic compound (e.g., $CaSO_4$, $Mg_m(PO_4)_n$). In one embodiment, a voltage difference is impressed, in a longitudinal direction or in a transverse direction, across an ionic liquid within the pore, and a varying ionic current through the pore, or a varying electron current across the pore (referred to collectively as an "electrical current") is measured in response to passage of each of an ordered sequence of polymer components, such as nucleotides in a nucleic acid or proteins, through the pore.

In one embodiment, the method includes steps of:

providing a pipette having a longitudinal axis and having a tapered region having a pore with a selected pore diameter in a range of 1-40 nanometers (nm);

providing a selected liquid in contact with an interior surface of the pore;

impressing a selected voltage difference across the selected liquid within the pipette pore substantially parallel to the pipette longitudinal axis direction, and providing an ionic current value induced in the selected liquid; and passing an unknown polymer molecule, having a sequence of polymer components, through the pore, and determining a change in the is ionic current signal induced by passage of each of the polymer components through the pore. In another embodiment, the voltage difference is impressed transversely, across the pore, and a transverse electronic current, induced in response to passage of each of the polymer components through the pore, is measured.

In another embodiment, a method for producing the pore includes steps of:

heating a hollow cylinder of a selected pipette material, having first and second cylinder ends, having a longitudinal axis and having a selected initial inner diameter, with a selected heating source for at least one of first and second longitudinal locations for at least one of first and second selected time intervals;

translating one of the first and second cylinder ends relative to the other of the first and second cylinder ends during a selected third time interval that partly or wholly overlaps at least one of the first time interval and the second time interval; and allowing the hollow cylinder to separate into at least first and second pipettes and at least one of the first and second pipettes has a pore with a pore diameter in a range 1-40 nanometers (nm).

DESCRIPTION OF BEST MODES OF THE INVENTION

Figure 1A:
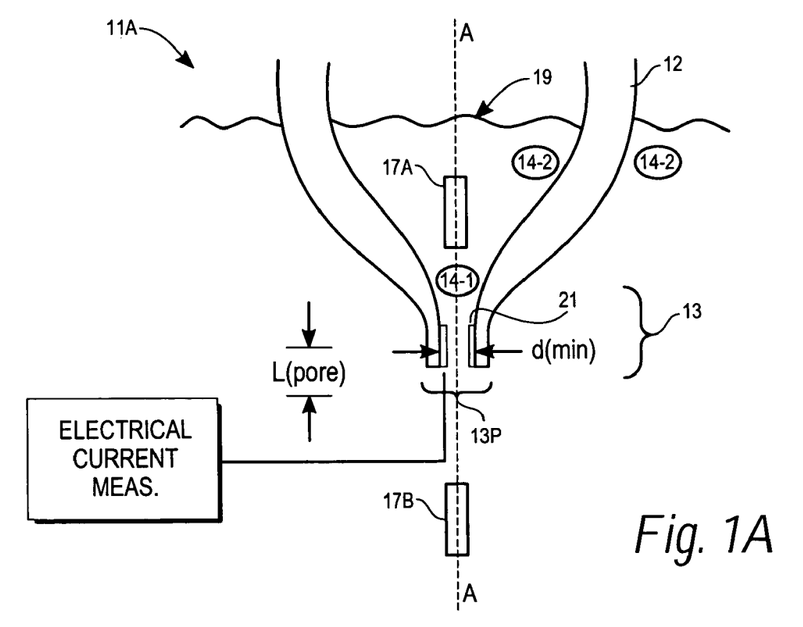
FIGS. 1A, 1B and 1C illustrate apparati for practicing the invention.

FIG. 1A illustrates one embodiment of apparatus for measurement of longitudinal ionic current in practicing the invention. The system 11 includes a glass pipette 12, having a longitudinal axis AA and having a tapered tip region 13, with a pore 13p having a selected pore minimum inner diameter d(min) in a preferred range of 1-40 nm, or larger if necessary. A length of the interior surface of the tip region 13 is provided with a selected first liquid 14-1 including an ionizable molecule including an alkali halide (NaCl, KCl, NaBr, KBr, $MgCl_2$, $CaCl_2$, MgClBr, etc.), ammonium compound (e.g., $NH_4$, $N(CH_3)_4$, or a suitable ionic organic compound or ionic inorganic compound (e.g., $CaSO_4$, $Mg_m(PO_4)_n$). A portion of the pipette adjacent to the pore is immersed in a selected second liquid 14-2, which may be, but need not be, the same as the first liquid 14-1. The pore 13p has a pore length L(pore) in a selected length range. A voltage difference ΔV, having a value in a range 10-2000 milliVolts, is impressed substantially in the longitudinal axis direction across the liquid in the pore, and an ionic current value IC through the pore is measured by an electrical current measurement module 15 The voltage difference may, for example, be provided by a first electrode 17A, positioned within the first liquid 14-1 in the interior surface of the pore 13p, and a second electrode 17B, positioned within a "bath" 19 of the second liquid 14-2 surrounding the pore. One or both of the electrodes, 17A and 17B, may include Ag/AgCl or another substance known to provide reversible current and to have low offset voltage in ionic solutions.

Figure 1B:
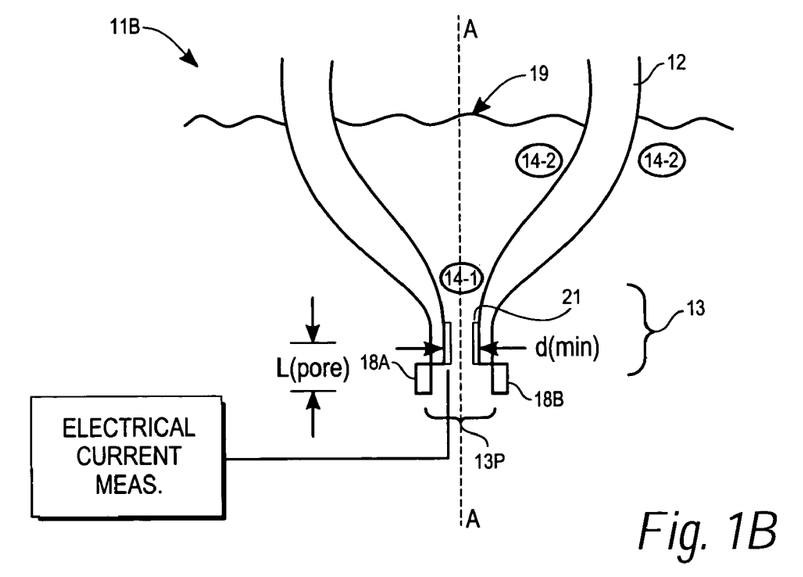

FIG. 1B, illustrating an embodiment for measuring transverse electronic current, is similar to FIG. 1A, except that spaced apart electrodes, 18A and 18B, replacing the electrodes 17A and 17B, are arranged on or adjacent to a perimeter of the pore 13 and an electronic current flows from 18A to 18B in response to imposition of a voltage difference ΔV between these electrodes.

Figure 1C:
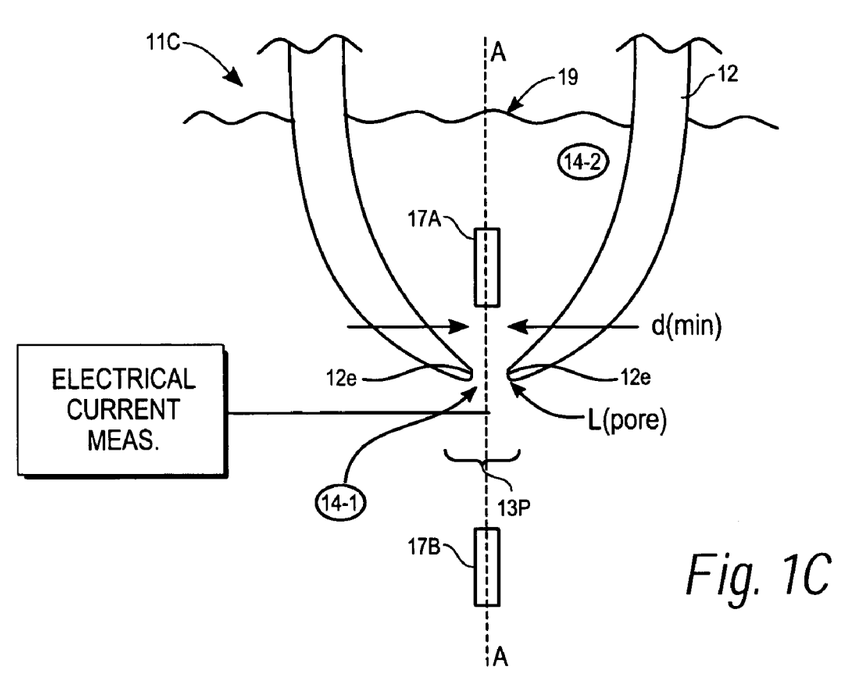

FIG. 1C illustrates a different configuration of the pore 13p, according to the invention. In FIG. 1C, different portions of an end 12e of the tip substantially face each other and define an effective pore length L(pore) that is approximately equal to a thickness of the pipette 12 at an end of the pipette. This configuration is preferred where the pore width d(min) is to be made as small as possible (e.g., less than or equal to 1.5 nm).

In one approach, an interior surface of the pore 13p is left uncoated in practicing the invention. Preferably, the interior surface of the pore 13p is coated or wetted or otherwise provided with a self-assembling monolayer ("SAM") 21 of a selected material that will manifest hydrogen bonding, van der Waals interaction and/or similar reversible, transient interactions with a class of polymers of interest. The SAM substance provided on an interior surface of the pore 13p may be octadecyltrichlorosilane ($C_{18}H_{37}SiCl_3$ or "OTS"), as discussed by Sagiv in "Organized Monolayers by Absorption. 1. Formation and Structure of Oleophobic Mixed Monolayers on Solid Surfaces," J. Amer. Chem. Soc. vol. 102 (1980) pp. 92-98, or may be another suitable substance that will interact with a polymer components passing through the pore 13p and allow measurement of a modulated ionic current signal or electron current signal that is characteristic of a particular polymer component. Other SAM substances that may be used include alkylsiloxane monolayers, alkylsilanes, trimethoxysilanes, mono-, di- and tri-chlorosilanes, octadecylsilanes, organochlorosilanes, aminosilanes, perfluorodecyltrichlorosilanes and aminopropylethoxysilanes.

From another perspective, a stable SAM can be formed using sulfur-containing absorbates on gold, chlorosilanes or alkoxysilanes on glass, and fatty acids on a metal oxide surface.

As used herein "SAM" includes an array of substantially identical molecules (e.g., containing a silane component) covalently attached to a glass surface and oriented substantially perpendicular to the surface, which interact, without permanent bonding, with a selected group of one or more solution molecules that pass near the SAM array. A SAM may be used to provide transient interactions with a polymer ubit passing through a nanopore and/or may be used to tailor the effective longitudinal and/or transverse dimensions (diameter, etc.) of a nanopore.

Formation of self-assembling monolayers on a gas or liquid interface were first reported by Langmuir in J. Am. Chem. Soc., vol. 39 (1917) 1848, and were first shown to be formable on a solid surface by Blodgett, J. Am. Chem. Soc., vol. 57 (1935) 1007. Spontaneous formation of a SAM on a solid substrate was first demonstrated by Bigelow, Pickett and Zisman, J. Colloid Interface Sci., vol. 1 (1946) 513 Chechik, Crooks and Stirling, in "Reactions and Reactivity in Self-Assembled Monolayers," Advanced Materials, 2000, 1161-1171, define a SAM as a monomolecular film of surfactant, formed spontaneously on a substrate upon exposure to a surfactant solution and provide a general review of use of SAMs. A SAM may be disordered or close packed, depending on the degree of wetting of the substrate surface. As noted by Chechik et al, ibid, a SAM is ideally suited as a scaffold to graft a polymer onto solid surfaces, because of the high density of functional groups, relatively small number of defects, and a well defined structure. A molecule that is part of a SAM may be terminated by various functional groups, such as OH and amines.

A second example of an SAM is (16-Mercapto)hexadecanoic acid (MHA) on a gold substrate, as studied and reported by J. Lahann et al in Science, vol. 239 (2003) pp 371-374. MHA includes hydrophobic chains capped by hydrophilic carboxylate end groups. Cleavage of the carboxylate end groups provides a low density SAM of hydrophobic chains. Application of a small electrical potential or voltage difference (e.g., $-1054$ mV$\leq$V$\leq$+654 mV to the negatively charged carboxylate groups provides an attractive force that causes a conformation change in the hydrophobic chains, whereby an all-trans conformation becomes partly trans and partly gauche conformation, with substantial qualitative and quantitative changes in associated sum-frequency generation (SFG) spectroscopic variations associated with the different conformations. The conformational changes are reversible so that removal of the applied electrical potential causes a return to the relatively featureless SFG spectroscopic variations associated with the original hydrophobic chain conformations (all trans). Viewed from another perspective, change in hydrophobic chain conformations associated with a specific change, such as a variation in translocation associated with passage of different polymer units through a nanopore in which a very thin layer of MHA on gold is provided, would cause a measurable change in electrical current or change in electrical potential (tens to hundreds of millivolts) associated with passage of each (different) polymer unit.

Figure 2A:
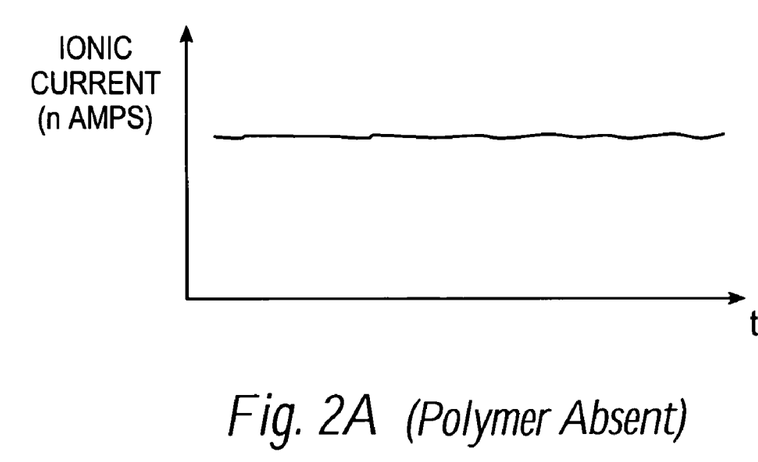
FIGS. 2A, 2B and 2C graphical views of typical sequences of ionic or electron current values measured with no polymer component present (2A), and in response to passage of a polymer component through a pore (2B, 2C).

In the absence of passage of a polymer component through the pore, a steady ionic current through the pore (or electronic current across the pore) will develop in response to impressing a small voltage difference in a longitudinal (or transverse) direction, as shown graphically in FIG. 2A.

Figure 2B:
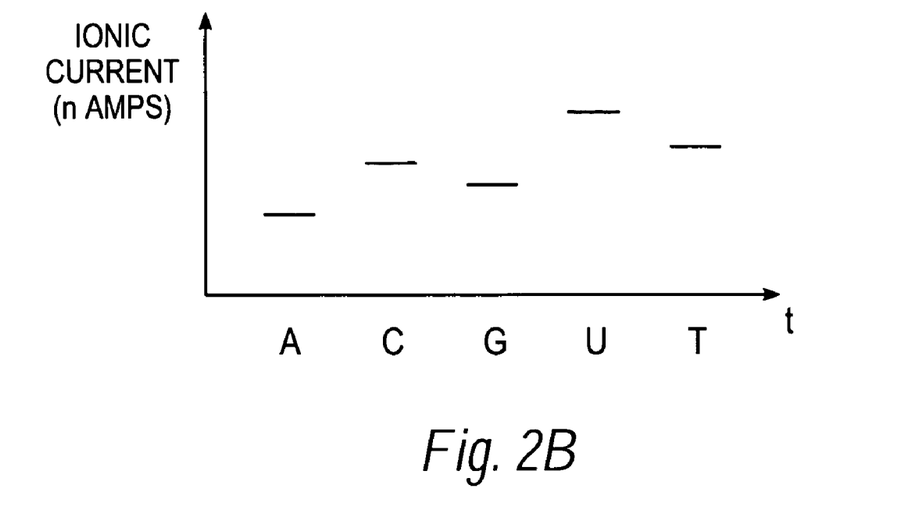
Figure 2C:
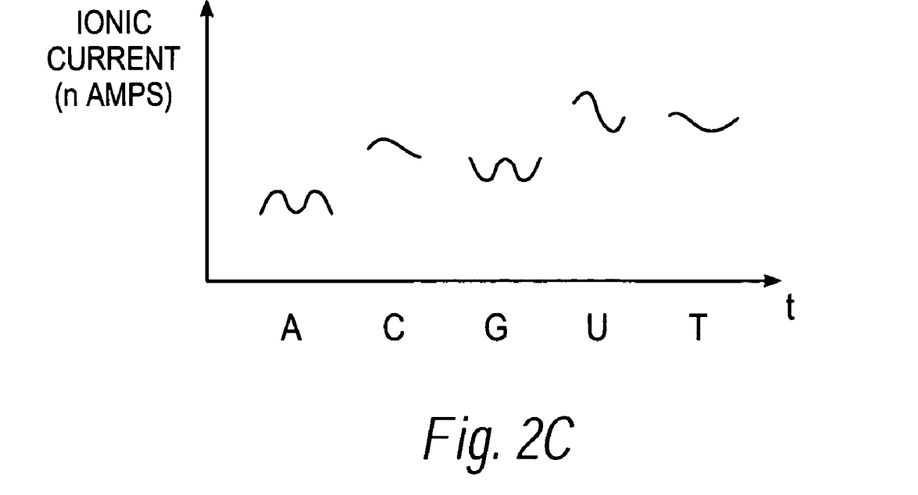

An ordered sequence of polymer components, such as a nucleic acid (e.g., DNA or RNA) is passed through the pore 13p, allowing development of a sequence of changing ionic current values, as illustrated in FIGS. 2B and/or 2C. In FIG. 2B, passage of each polymer component through the pore 13p is assumed to produce an approximately square wave signal, having an approximately constant characteristic amplitude for a small time interval that corresponds to the time required for that polymer component to pass through the tip. In FIG. 2C, passage of each polymer unit through the pore 13p is assumed, more realistically, to produce a signal having a characteristic, time varying signal shape, a characteristic average amplitude and a characteristic shape parameter, for a small time interval that corresponds to the time required for that polymer component to pass through the tip.

Where one or more polymer components passes through the pore, translocation will cause the steady ionic current shown in FIG. 2A to change with time in response to passage of the polymer component through the pore and the accompanying translocation. If, for example, the polymer sequence is a nucleic acid, such as DNA (alternatively, RNA), each nucleotide will contain one of the four bases adenine (A), cytosine (C), guanine (G) and thymine (T) (alternatively, adenine, cytosine, guanine and uracil (U) for RNA). Ideally, each of the four bases (for DNA or for RNA) will produce a distinguishable change in ionic current signal as that nucleotide passes through the pipette tip, as suggested in FIG. 2B or FIG. 2C.

Under the influence of an applied voltage difference, negatively charged nucleotides or other polymer units are driven through the pore, and a polynucleotide strand can thus be threaded from one side of a lipid biolayer to the other. A steady electrical current that is present in the pore in the absence of a polymer unit is partly occluded during translocation. In principle, polymer units of different lengths can be distinguished from each other by translocation duration, and several homopolymers of different composition can be distinguished based on characteristic levels of electrical current reduction.

Figure 3:
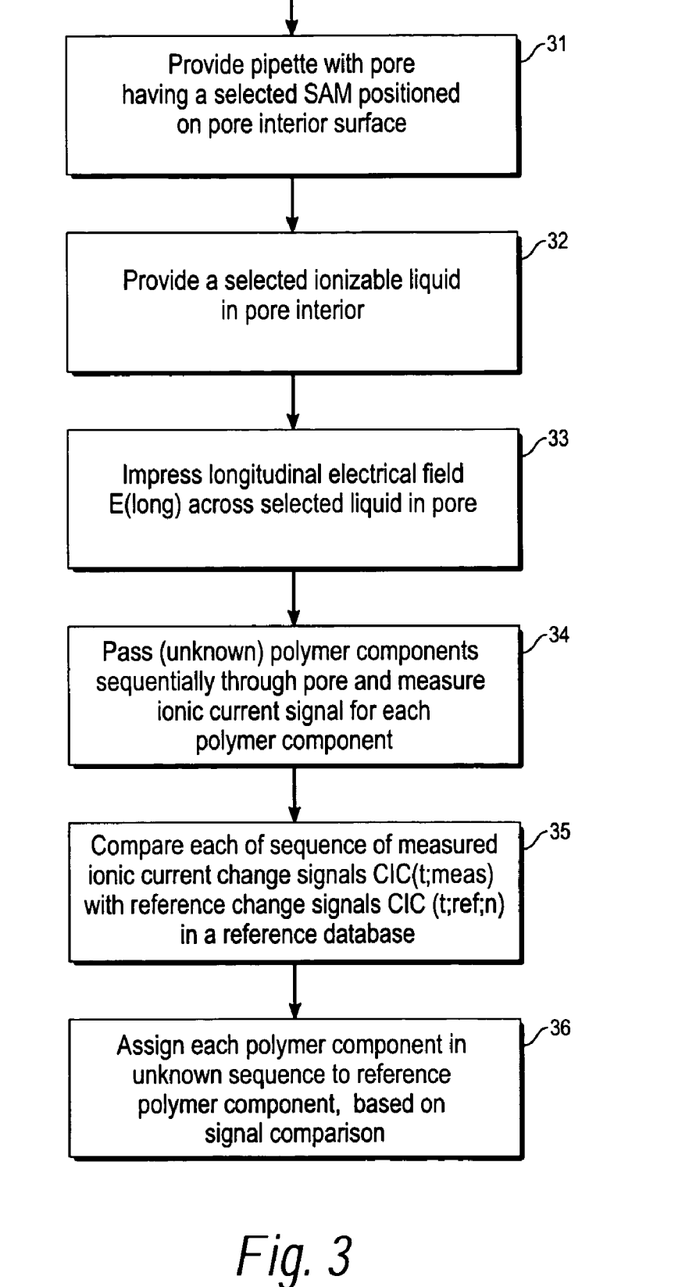
FIGS. 3, 4 and 5 are flow charts illustrating procedures for practicing the invention according to two embodiments.

FIG. 3 is a flow chart of a procedure for practicing the invention. In step 31 of FIG. 3, a pipette, having a longitudinal axis and having a tapered tip with an associated pore having a selected pore minimum inner diameter d in a preferred range (e.g., d=1-40 nm) is provided, and a selected self-assembling monolayer (SAM) is optionally provided on some portion of the pore surface. In step 32, a selected first liquid containing ions is provided in the interior surface of the pore, preferably containing an alkali halide, ammonium compounds (e.g., $NH_4$, $N(CH_3)_4$, or a suitable ionic organic compound or ionic inorganic compound (e.g., $CaSO_4$, $Mg_m(PO_4)_n$). More generally, the selected first liquid may be any solution that provides a concentration ρ of ions at least equal to a threshold value ρ(ion;thr), for example, ρ(ion;thr)≧$10^x$ $cm^{-3}$. The liquid may include the polynucleotide or other polymer that is to be identified. In step 33, a voltage difference having a value in a range ΔV=10-2000 milliVolts is impressed on the liquid in the pore, in a direction substantially parallel to the pipette longitudinal axis. If the polymer has a net electrical charge, the polarity of the voltage difference is chosen to induce the polymer to pass through (or across) the pore. In step 34, ordered components in a polymer (unknown) are sequentially passed through the pore, and each of a sequence of changes in ionic current signals is measured, resulting in a sequence of measured values such as the sequences shown in FIG. 2B or FIG. 2C.

In step 35 (optional), the sequence of changes in measured ionic current signals CIC(t;meas) is compared, one-by-one or in consecutive groups, with reference change signals CIC(t;ref;n), numbered n=1, . . . , N(N≧2) in a reference signal database. Each reference change signal corresponds to a reference polymer component. In step 36 (optional), each polymer component (e.g., a nucleotide containing a particular base) in the unknown sequence is assigned to the reference polymer component having a reference ionic current change signal that is most similar, in some quantitative sense, to the measured (changes in) ionic current change signal. Optionally, steps 35 and 36 are performed off-line The signal comparison step 35 is optionally implemented as follows. The ionic current change signal CIC(t;meas) for the unknown polymer sequence is measured at a sequence of time values $t_m$, producing a sequence of measured ionic current change values $\{CIC(t_m;meas)\}_m$. (m=1, . . . , M; M≧2) This sequence of measured ionic current change values is compared with a reference sequence (n) of ionic current change signal values $\{CIC(t_m+\tau(n);ref;n)\}_m$, where τ(n) is a selected time shift that may vary with the reference number n being considered, by computing an error value $$\varepsilon(n) = \left\{ \sum_{m=1}^{M} w_m |CIC(t_m; meas) - CIC(t_m + \tau(n); ref; n)|^p \right\}^{1/p}, \quad (1)$$

where $\{w_m\}_m$ is a selected sequence of non-negative weight values (at least one positive) and p is a selected positive number (e.g., p=1, 1.6 or 2). Reference ionic current change signals CIC($t_m$+τ;ref;n) for which the error satisfies ε(n)>ε (thr), where ε(thr) is a selected positive threshold value, are discarded and not considered further for this measured ionic current change value sequence $\{CIC(t_m;meas)\}_m$. When at least one error value satisfies ε(n)≦ε(thr), the "surviving collection"

$$SC=\{CIC(t_m+\tau(n);ref;n) | \varepsilon(n) \leq \varepsilon(thr)\} \quad (2)$$

of all reference signals with error values that satisfy the inequality ε(n)≦ε(thr), are considered, and the reference ionic current change signal CIC($t_m$+τ(n);ref;n) that provides the smallest error ε(n) is assigned to the unknown polymer unit. When the surviving collection SC is an empty set, because no error value satisfies ε(n)≦ε(thr), the system assigns a selected symbol, such as UNK, to this polymer unit.

Figure 4:
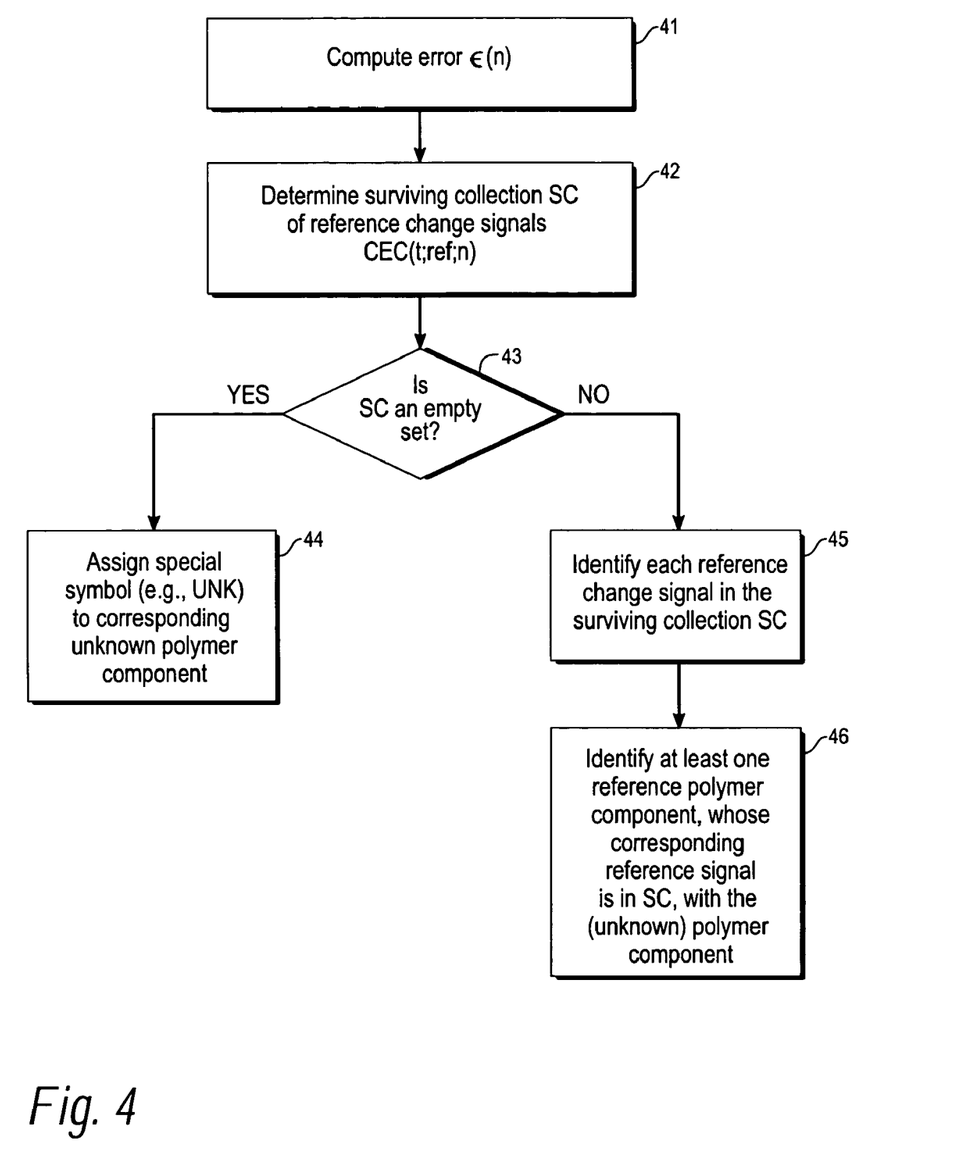

The comparison procedure can be summarized in a flow chart in FIG. 4. In step 41, the error ε(n), defined as in Eq. (1) or in another suitable manner, for each reference change signal CIC($t_m$+τ(n);ref;n) in the database is computed. In step 42, the surviving collection SC of reference signals is determined. In step 43, the system determines if SC is an empty set. If the answer to the query in step 43 is "yes," the system assigns a special symbol (e.g., UNK) to the corresponding measured ionic current value in step 44, indicating that no reference change signal IC($t_m$+τ(n);ref;n) is sufficiently similar to the measured ionic current change signal. If the answer to the query in step 43 is "no" (SC is non-empty), the system identifies, in step 45, each reference change signal CIC($t_m$+τ (n);ref;n=n') for which the corresponding error satisfies $$\varepsilon(n')=\min_{1 \leq n \leq N} \varepsilon(n). \quad (3)$$

In step 46, the system identifies at least one reference polymer component, for which the corresponding reference change signal CIC($t_m$+τ(n');ref;n') is in the surviving collection SC, with the unknown polymer component whose signal was measured.

Figure 5:
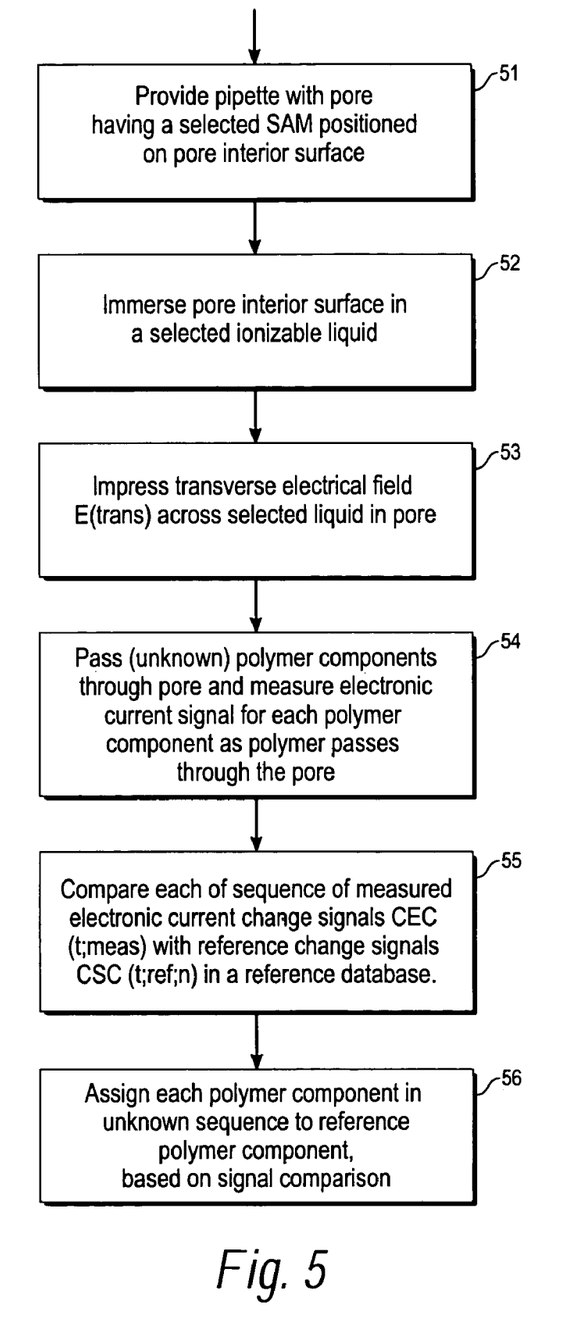

FIG. 5 is a flow chart of an alternate procedure for practicing the invention, using a transverse voltage difference. In step 51 of FIG. 5, a pipette, having a longitudinal axis and having a tapered tip with an associated pore having a selected pore minimum inner diameter d in a preferred range (e.g., d=1-40 nm) is provided, where a selected self-assembling monolayer is optionally provided on an interior surface of the pore. In step 52, the pore interior is provided with a selected first liquid, preferably containing an alkali halide, ammonium compounds (e.g., $NH_4$, $N(CH_3)_4$, or a suitable ionic organic compound or ionic inorganic compound (e.g., $CaSO_4$, $Mg_m(PO_4)_n$), so that the first liquid is present within the pore. More generally, the selected liquid may be any solution that provides at least a concentration ρ of electrons at least equal to a threshold value ρ(ion;thr), for example, $\rho(ion;thr) \geq 10^x\ cm^{-3}$. In step 53, a voltage difference having a value in a range ΔV=10-2000 milliVolts, or more if desired, is impressed on the first liquid in the pore, in a direction substantially transverse to the pipette longitudinal axis. In step 54, a polymer sequence (unknown) is sequentially passed through the pore, and each of a sequence of electron current change signals is measured, resulting in a sequence of measured values such as the sequences shown in FIG. 2B or FIG. 2C. The electron signals resulting from imposition of the transverse voltage difference are likely to be different from the corresponding ionic current signals resulting from imposition of a longitudinal voltage difference.

In step 55 (optional), the sequence of measured electron current change signals $CEC(t_m;meas)$ is compared, one-by-one or in consecutive groups, with reference change signals $CEC(t_m+\tau(n);ref;n)$, numbered n=1, . . . , N' (N'≧2) in a reference signal database. In step 56 (optional), each polymer unit (e.g., a nucleotide containing a particular base) in the unknown sequence is assigned to the reference polymer component having a reference electron current value that is most similar to the measured electron current signal. Step 55 may, for example, be implemented by analogy with implementation of step 35 in FIG. 3, with electronic change signals, $CEC(t_m;meas)$ and $CEC(t_m+\tau(n);ref;n)$ replacing the corresponding ionic current change signals in Eqs. (1) and (2).

Figure 6A:
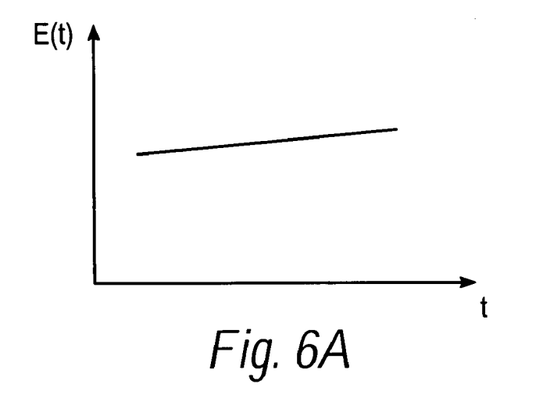
FIGS. 6A-6F graphically illustrate time variations that can be applied to an impressed voltage difference used in the invention.
Figure 6B:
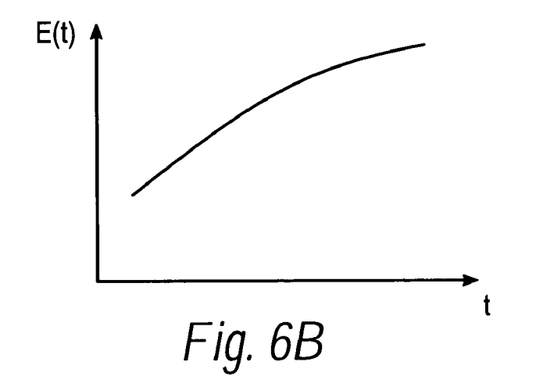
Figure 6C:
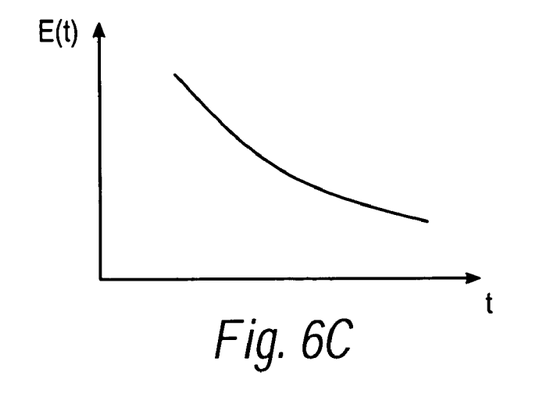
Figure 6D:
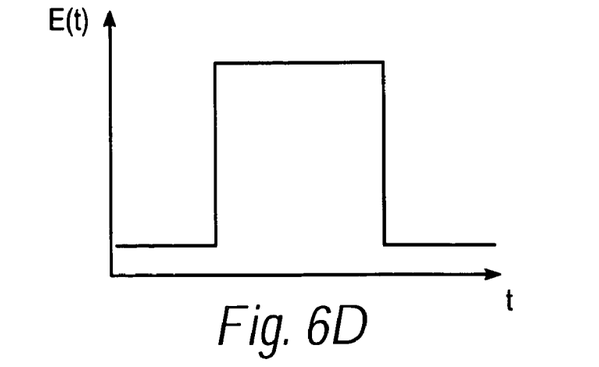
Figure 6E:
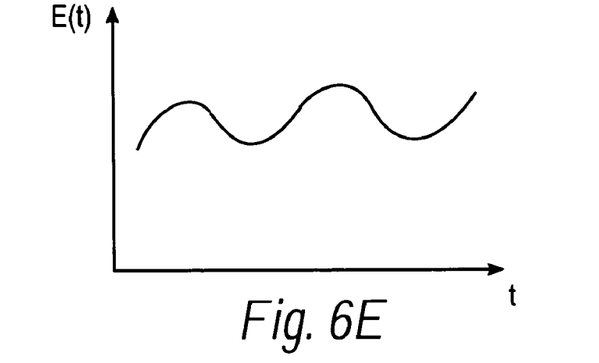
Figure 6F:
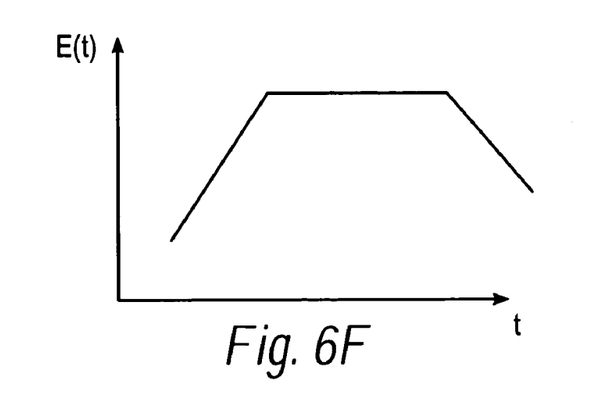

The voltage difference amplitude ΔV(t), impressed longitudinally or transversely across the selected liquid, may be substantially uniform in time, as illustrated in FIG. 6A, may be substantially monotonically increasing in time (FIG. 6B), may be substantially monotonically decreasing in time (FIG. 6C), may be substantially a step function in time (FIG. 6D), may vary substantially sinusoidally in time (FIG. 6E), may vary substantially trapezoidally in time (FIG. 6F), with temporal length segments τ1, τ2 and τ3, or may have another suitable time varying shape. The trapezoidal variation shown in FIG. 6F includes a triangular variation, in which the middle segment has length τ2=0.

Figure 7A:
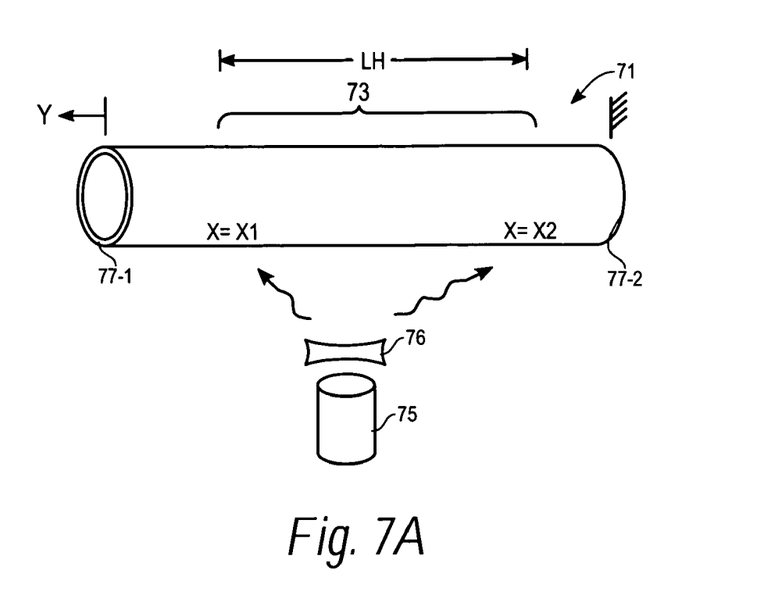
FIGS. 7A and 7B illustrate formation of a pipette tip for use in the invention.
Figure 7B:
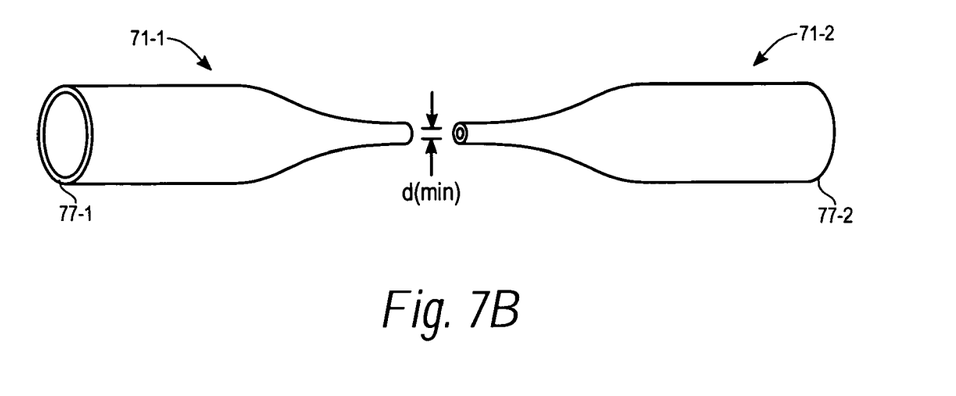

A tip region of a pipette (quartz glass, aluminosilicate glass, borosilicate glass or other suitable glass) having an appropriate minimum inner diameter may be formed using the following procedure, illustrated in FIGS. 7A and 7B. A selected middle region 73, having a preferred length LH in a range 0.1-2 cm or more, of a pipette 71 with a hollow core is heated or otherwise receives substantial thermal energy, using a laser, infrared source or a heated metal filament 75 and (optional) associated focusing system 76, at one or more locations, x=x1, x=x2, etc., for one, two or more time intervals, of length Δt1, Δt2, etc. The time intervals may partly or wholly overlap or may be isolated from each other. As the heating or irradiation continues, one or both of first and second ends, 77-1 and 77-2, of the pipette is pulled with a selected force F, optionally $10^1$-$10^7$ dynes or more, or at a selected displacement rate, v of a few mm/sec, so that the first and second ends are displaced relative to each other. The pipette 71 separates into two pipette segments, 71-1 and 71-2, in the (last) heating cycle, and at least one of the two resulting pipette segments has a hollow core (a pore) with a pore minimum inner diameter d(min). Tip parameters (thickness, nanopore diameter, nanopore length, etc.) can be partly controlled by appropriate choice of one or more of the parameters heating rate, LH, Δt(irr), F and/or v.

Suitable applications of the invention, using ionic current or electronic current, include the following: (1) counting of genomic or non-genomic fragments, by identification of a first end and/or a second end of each fragment that passes through a nanopore; (2) identification of locations of single strand segments and double strand segments in a "mixed" DNA sequence passing through a nanopore; (3) discrimination between single strands and double strands of DNA passing through a nanopore; and (4) identification of individual nucleotides in single strand DNA passing through a nanopore; (5) identification of corresponding base pairs (e.g., cytosine-guanine, adenine-thymine and adenine-uracil) in a double strand DNA or RNA passing through a nanopore, and (6) estimation of polymer component length by correlation with length of time interval for translocation.

What is claimed is:

1. A method for obtaining a reading of a sequence of components in a polymer molecule, the method comprising:
   providing a pipette having a longitudinal axis and having a tapered region and having a pore with a selected pore diameter in a range of 1-40 nanometers (nm);
   providing a selected liquid in contact with an interior surface of the pore;
   impressing a selected voltage difference across the selected liquid within the pipette pore substantially parallel to the pipette longitudinal axis direction, and providing an ionic current value induced in the selected liquid;
   passing a polymer molecule, having a sequence of two or more polymer components, through the pore, and determining a change in the ionic current signal induced by passage of each of the polymer components through the pore;
   comparing each of the sequence of changes in ionic current signals with each of N reference ionic current change signals (N≧2), with each reference ionic current change signal corresponding to a reference polymer component drawn from a reference group of polymer components; and
   for at least one of the determined changes in ionic current signals for one of the polymer components, identifying the polymer component with the reference polymer component whose reference ionic current change signal is closest to the at least one determined ionic current change signal.

2. The method of claim 1, further comprising providing a self-assembling monolayer of a selected substance on a selected portion of said interior surface of said pore.

3. The method of claim 2, further comprising choosing said self-assembling monolayer to include at least one of: (i) octadecyltrichlorosilane on glass and (ii) (16-Mercapto)hexadecanoic acid on a gold substrate.

4. The method of claim 1, further comprising choosing said polymer sequence to be a nucleic acid sequence including the bases adenine, cytosine and guanine and at least one of the bases thymine and uracil.

5. The method of claim 1, further comprising selecting material for said pipette from a group of materials including quartz glass, aluminosilicate glass and borosilicate glass.

6. The method of claim 1, further comprising choosing said selected liquid to include at least one of an alkali halide, an ammonium compound, an ionic organic compound and an ionic inorganic compound.

7. The method of claim 1, further comprising providing a selected second liquid in contact with a portion of a surface of said pipette not including said interior surface of said pore.

8. The method of claim 7, further comprising choosing said second liquid to be substantially the same as said selected first liquid.

9. The method of claim 7, further comprising choosing said second liquid to be different from said selected first liquid.

10. The method of claim 1, wherein said process of identifying said polymer component with said reference polymer component whose reference ionic current signal is closest to said at least one determined ionic current signal comprises:
 (i) measuring a value CIC($t_m$;meas) of said determined ionic current change signal at each of a sequence of times t=$t_m$ (m=1, ..., M;M≧1);
 (ii) forming an error value, defined as $$\varepsilon(n) = \left\{ \sum_{m=1}^{M} w_m |CIC(t_m; meas) - CIC(t_m; +\tau(n); ref; n)|^p \right\}^{1/p},$$

between said determined ionic current change signal value and a corresponding reference ionic current change signal value, for each of N reference ionic current change signals CIC($t_m$;+τ(n);ref;n), numbered n=1, ..., N(N≧2), where $\{w_m\}_m$ is a set of selected non-negative weight values, τ(n) is a selected time shift value and p is a selected positive number; and
 (iii) when at least one reference ionic current signal, numbered n', satisfies ε(n')≦ε(thr), where ε(thr) is a selected threshold value, identifying at least one reference polymer component, number n", with said polymer component, where ε(n")=$\min_{1 \leq n \leq N}$ε(n).

11. The method of claim 1, further comprising passing said polymer sequence through said tapered tip of said pipette at an average rate in a range of 10-1000 polymer components per millisecond.

12. The method of claim 1, further comprising selecting said voltage difference from a group of time-dependent differences including a difference that (i) is substantially uniform in time; (ii) increases substantially monotonically with time; (iii) decreases substantially monotonically with time; (iv) is substantially a step function in time; (v) varies substantially sinusoidally with time; and (vi) varies substantially trapezoidally with time.

13. A method for obtaining a reading of a sequence of components in a polymer molecule, the method comprising:
 providing a pipette having a longitudinal axis and having a tapered region and having a pore with a selected pore diameter in a range of 1-40 nanometers (nm), where a self-assembling monolayer of a selected substance is provided on an interior surface of the pore;
 providing a selected liquid in contact with an interior surface of the pore;
 impressing a selected voltage difference across the selected liquid within the pipette pore transverse to the pipette longitudinal axis direction, and providing an electronic current value induced in the selected liquid;
 passing a polymer molecule, having a sequence of two or more polymer components, through the pore, and determining a change in the electronic current signal induced by passage of each of the polymer components through the pore
 comparing each of the sequence of changes in electronic current signals with each of N reference electronic current change signals (N≧2), with each reference electronic current change signal corresponding to a reference polymer component drawn from a reference group of polymer components; and
 for at least one of the determined changes in electronic current signals for one of the polymer components, identifying the polymer component with the reference polymer component whose reference electronic current change signal is closest to the at least one determined electronic current change signal.

14. The method of claim 13, wherein where a self-assembling monolayer of a selected substance is provided on a selected portion of said interior surface of said pore.

15. The method of claim 14, further comprising choosing said self-assembling monolayer to include at least one of: (i) octadecyltrichlorosilane on glass and (ii) (16-Mercapto) hexadecanoic acid on a gold substrate.

16. The method of claim 13, further comprising choosing said polymer sequence to be a nucleic acid sequence including the bases adenine, cytosine and guanine and at least one of the bases thymine and uracil.

17. The method of claim 13, further comprising selecting material for said pipette from a group of materials including quartz glass, aluminosilicate glass and borosilicate glass.

18. The method of claim 13, further comprising choosing said selected liquid to include at least one of an alkali halide, an alkaline halide, a nitrate and a sulfate.

19. The method of claim 13, further comprising providing a selected second liquid in contact with a portion of a surface of said pipette not including said interior surface of said pore.

20. The method of claim 19, further comprising choosing said second liquid to be substantially the same as said selected first liquid.

21. The method of claim 19, further comprising choosing said second liquid to be different from said selected first liquid.

22. The method of claim 13, wherein said process of identifying said polymer component with said reference polymer component whose reference electronic current change signal is closest to said at least one determined electronic current signal comprises:
 (i) measuring a value CEC($t_m$;meas) of said determined electronic current change signal at each of a sequence of times t=$t_m$, (m=1, ..., M;M≧1);
 (ii) forming an error value, defined as $$\varepsilon(n) = \left\{ \sum_{m=1}^{M} w_m |CEC(t_m; meas) - CEC(t_m; +\tau(n); ref; n)|^p \right\}^{1/p},$$

between said determined electronic current change signal value and a corresponding reference electronic current change signal value, for each of N reference electronic current change signals CEC($t_m$;+τ(n);ref;n), numbered n=1, ..., N(N≧2), where $\{w_m\}_m$ is a set of selected non-negative weight values, τ(n) is a selected time shift value and p is a selected positive number; and
 (iii) when at least one reference ionic current change signal, numbered n', satisfies ε(n')≦ε(thr), where ε(thr) is a selected threshold value, identifying at least one reference polymer component, number n", with said polymer component, where ε(n")=$\min_{1 \leq n \leq N}$ε(n).

23. The method of claim 13, further comprising passing said polymer sequence through said tapered tip of said pipette at an average rate in a range of 10-1000 polymer components per millisecond.

24. The method of claim 13, further comprising selecting said voltage difference from a group of time-dependent differences including a difference that (i) is substantially uniform in time; (ii) increases substantially monotonically with time; (iii) decreases substantially monotonically with time; (iv) is substantially a step function in time; (v) varies substantially sinusoidally with time; and (vi) varies substantially trapezoidally with time.

* * * * *